United States Patent
Das et al.

(10) Patent No.: US 7,709,692 B2
(45) Date of Patent: May 4, 2010

(54) PROCESS FOR THE PRODUCTION OF PARA-DIETHYLBENZENE

(75) Inventors: Jagannath Das, Gujarat (IN); Pavagada Raghavendra Char, Gujarat (IN); Arun Gurudath Basrur, Gujarat (IN); Anand Bhimarao Halgeri, Gujarat (IN); Sanjay Ramakrishna Rinke, Maharashtra (IN); Laxmilal Jain, Maharashtra (IN); Avinash Ramchandra Saple, Maharashtra (IN); Mantri Ganapati, Maharashtra (IN)

(73) Assignee: Indian Petrochemicals Corporation Limited, Gujarat (IN)

( * ) Notice: Subject to any disclaimer, the term of this patent is extended or adjusted under 35 U.S.C. 154(b) by 1144 days.

(21) Appl. No.: 11/333,810

(22) Filed: Jan. 17, 2006

(65) Prior Publication Data

US 2006/0173225 A1 Aug. 3, 2006

(51) Int. Cl.
*C07C 2/66* (2006.01)
*C07C 6/12* (2006.01)

(52) U.S. Cl. ........................... 585/467; 585/475

(58) Field of Classification Search ................. 585/467, 585/475
See application file for complete search history.

(56) References Cited

U.S. PATENT DOCUMENTS 5,406,015 A * 4/1995 Beck et al. .................. 585/475

* cited by examiner

*Primary Examiner*—Thuan Dinh Dang
(74) *Attorney, Agent, or Firm*—Ladas & Parry LLP

(57) ABSTRACT

The present invention relates to a process for the selective production of para-diethyl benzene from a mixed aromatic feedstock containing ethyl benzene and at least one other aromatic compound selected from benzene, alkylated benzene having alkyl group with carbon number 1 to 6, monoalkyl aromatics, dialkyl aromatics, trialkyl aromatics, tetraalkyl aromatics, pentaalkyl aromatics, hexaalkyl aromatics, containing side chains having 1 to 6 carbon atoms, and any mixtures thereof, the process comprising of (a) alkylating the feedstock under alkylating conditions, over a selectivated metallosilicate composite catalyst; and (b) recovering a product stream containing at least 95 wt % para-diethyl benzene, the product stream being substantially free from other isomers of diethylbenzene, $C_8$ aromatics, $C_9$ aromatics, $C_{10}+$ heavy aromatics other than diethyl benzene isomers, sulphur, halogen, olefinic compound and carbonyl compounds.

27 Claims, 2 Drawing Sheets

PROCESS FOR THE PRODUCTION OF PARA-DIETHYLBENZENE

FIELD OF THE INVENTION

Figure 1:
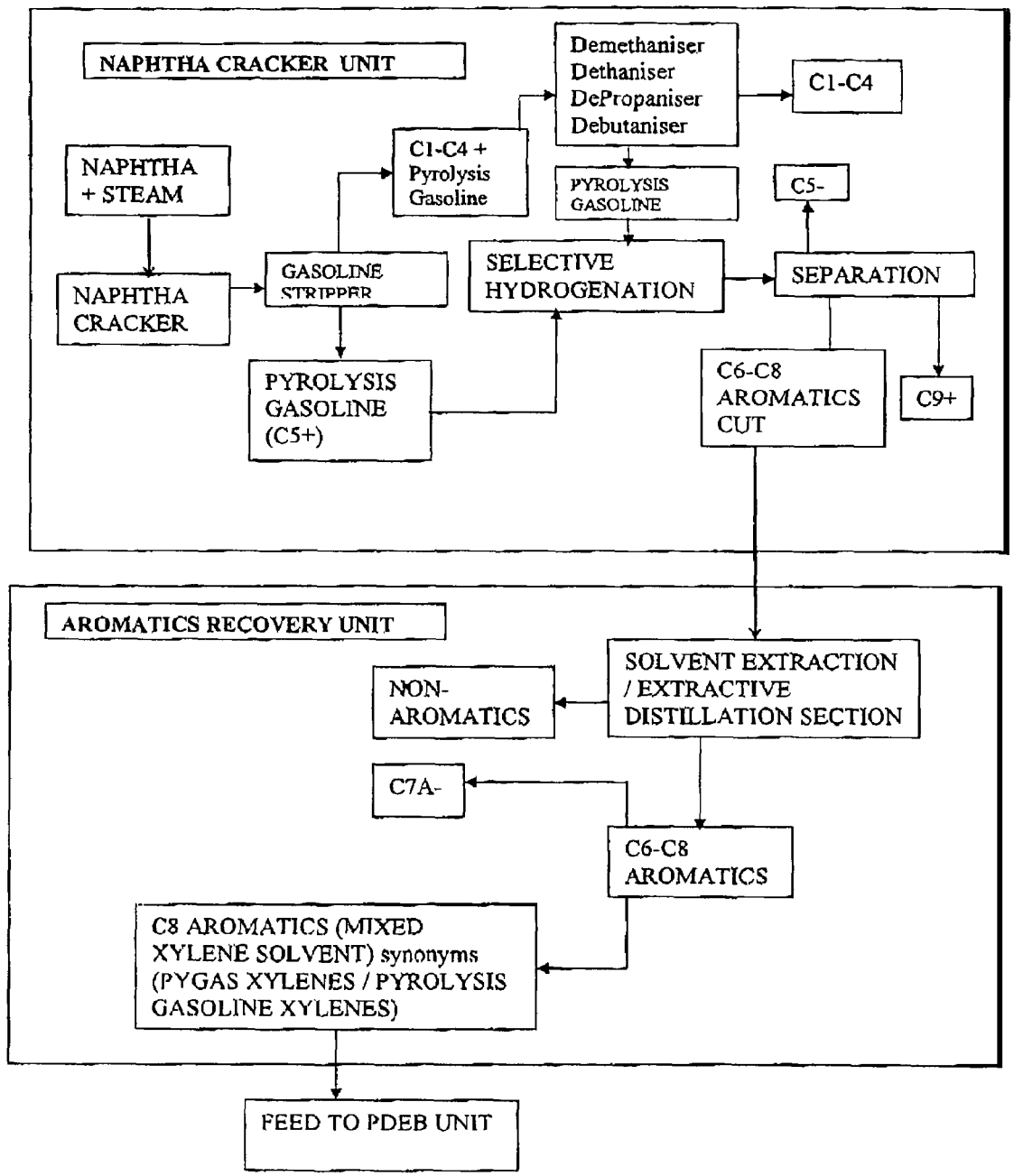

The present invention relates to a process for production of para-diethylbenzene. More specifically the present invention relates to a process for selective production of para-diethylbenzene using a reactant stream rich in ethylbenzene, such as a $C_8$ aromatic stream, (mixed xylene stream from pyrolysis gasoline or pygas aromatic stream). In particular the present invention comprises of producing para-diethylbenzene, suitable for commercial applications, by contacting the said reactant stream ($C_8$ aromatics stream consisting of mainly ethylbenzene and xylenes from pyrolysis gasoline or pygas aromatic stream) and optionally an ethylating agent in the presence of a selectivated metallosilicate composite catalyst under specified conditions of operations, recovering the para-diethylbenzene and heavier hydrocarbon from reactor effluent by any known manner, treating the recovered para-diethylbenzene along with or without heavy $C_{10}+$ aromatics product stream with suitable clay material under specified conditions of operation to remove olefinic impurities, and finally recovering pure para diethylbenzene product from the clay treated effluent.

BACKGROUND OF THE INVENTION

Diethylbenzenes have three isomers namely ortho-, meta- and para-. The para isomer is industrially more important than the other two isomers. It is a high value chemical having immense industrial importance by virtue of its utility as a desorbent in the selective recovery of para-xylene from isomeric $C_8$ raffinate, by well known "PAREX" process innovated by M/s Universal Oil Product (USA). The demand for para-diethylbenzene is bound to increase in the coming years with the continuous growth in para-xylene demand.

Diethylbenzenes can be conveniently synthesized by using existing alkylation catalysts like $AlCl_3$, HF, $BF_3$ etc. However, conventional catalyst is not selective to the para-isomer, Isomers of aforesaid ortho-, meta- and para-diethylbenzene can result in equilibrium concentration according to thermodynamics. Thermodynamic equilibrium composition of the three isomers at about 425° C. is as follows: ortho-diethyl benzene:meta-diethyl benzene:para-diethyl benzene=19:54:27. These isomers have very close boiling points to each other and the relative volatility is nearly one. Hence separation is difficult and is quite expensive. In addition, with $AlCl_3$ type catalyst, not only is separation difficult, it is impossible to avoid loss of raw material due to multiple alkylation giving polyalkylated heavy products. Moreover, due to strong acidity, disposal of catalyst causes serious environmental pollution apart from corrosion of equipments during operation of the process. Another approach for producing para-diethyl benzene is through adsorptive separation of para-isomer from mixed diethyl benzene isomers, which are produced during ethylbenzene/styrene manufacture.

Solid acid catalysts, particularly zeolites have been known to be very useful to replace the earlier $AlCl_3$, HF, $BF_3$ type catalysts. A new type of zeolite catalyst, which is known as ZSM-5, was discovered by Mobil Oil Corporation in 1972, has been used for many petrochemicals and hydrocarbon processes. The particulars of the method of production of the catalyst are disclosed in U.S. Pat. No. 3,702,886 and the details of the alkylation processes are revealed in an article published in the "Oil and Gas Journal, Sep. 26, 1977 by P. J. Lewis. The pores of this sort of zeolites have a uniform aperture. Therefore, hydrocarbons smaller than the pore dimensions are adsorbed and larger hydrocarbons are rejected. Hence it is frequently referred to as a "molecular sieve". These materials are known to possess "reactant selectivity", "product selectivity" and "transition selectivity". Details about the different kind of selectivity as exhibited by these materials are described in the book "Shape Selective Catalysis in Industrial Applications" Second Edition, by N. Y. Chen, W. E. (Garwood, F. G. Dwyer, Marcel Dekker, Inc., 1996. There are many precedents in industry making use of these characteristics to conduct chemical reaction, but usually in a given process only one kind of selectivity is achieved at a time, viz., either reactant selectivity, or product selectivity or transition state selectivity. The ZSM-5 zeolite catalyst is characterized by its selectivity, being able to satisfy the needs for high selectivity to products of different molecules, but it still falls short of expectation in respect of isomers of same kind of product. For instance, when toluene is alkylated with methanol over ZSM-5 zeolite catalyst, selectivity for xylenes are very high, but the ratio of isomers of xylenes namely ortho, meta- and para-xylene remains near thermodynamic equilibrium compositions. The details are reported in J. of Catalysis. Vol 67, page 159, 1981 by W. W. Kaeding et.al.

Various techniques to enhance shape selectivity of medium pore aluminosilicates have been reported. U.S. Pat. Nos. 4,086,287; 4,094,921 and 4,117,024 describe catalytic processes for selective ethylation of monoalkylbenzene (toluene, ethylbenzene) to produce para ethyltoluene, para-diethylbenzene, using crystalline aluminosilicate zeolite ZSM-5 modified with oxides of phosphorus, antimony, boron, magnesium and/or steaming and coking. U.S. Pat. Nos. 4,117,026 and 4,128,592 describe catalytic processes for the selective production of para dialkyl substituted benzenes contain alkyl group having 1 to 4 carbon atoms using aluminosilicate zeolite modified with difficultly reducible oxides and further modified by coking. Similar processes have also been described in U.S. Pat. 4,143,084. Catalysts and processes for selective production of para-dialkyl substituted benzenes have been described in U.S. Pat. Nos. 4,379,761 and 4,465,886. The catalyst as described in U.S. Pat. No. 4,379,761 comprises a porous crystalline aluminosilicate zeolite ZSM-5 having deposited silica thereon and having incorporated there in phosphorus. U.S. Pat. No. 4,465,886 describes the selective conversion of certain hydrocarbon feed stock to product rich in para-dialkyl substituted benzene over a catalyst composite comprising of crystalline aluminosilicate zeolite ZSM-5 having deposited there on a coating of silica which extensively covers and resides substantially exclusively on the external surface there of. U.S. Pat. No. 4,465,886 teaches that the charge stock used for the selective production of para dialkyl substituted benzene includes a hydrocarbon precursor selected from the group consisting of mono-alkyl substituted benzene having 1-4 carbon atoms in the alkyl substitutent, such as toluene, ethylbenzene, propylbenzene or butylbenzene and a mixture of such precursor or benzene with an alkylating agent containing from 1to 4 carbon atoms, (see col.10 lines 3-12). It also teaches that 'The use of mixed aromatics as feed is also possible'. For example a mixture of ethylbenzene and toluene is converted selectively to a mixture rich in para-dialkyl substituted benzene such as para diethylbenzene and para ethyltoluene, the latter predominating at high toluene to ethylbenzene ratios in the feed" (see column 10, lines 22-27). Similar teaching are also described in U.S. Pat. No. 4,421,941 col. 12, lines 40-49; col.12. lines 59-64 and in U.S. Pat. No. 4,477,583 vol. 10. lines 3-12, and col.10, lines 22-27

Thus the aforementioned art describes simultaneous alkylation of a mixed aromatics feed to produce individual para-disubstituted product depending on the components in the feed mixture. Based on the above teaching, it is completely non-obvious to consider a feed mixture wherein a particular component of the mixture is selectively alkylated, while other components remains largely unaffected. For example, consideration of a $C_8$ aromatics stream contain primarily ethylbenzene and xylenes, wherein ethylbenzene is disproportionate or alkylated over a selectivated metallosilicate catalyst, to produce para-diethylbenzene while the xylene isomers in the mixture remain substantially unaffected.

U.S. Pat. No. 4,613,717 describes process for producing 1,4-dialkylbenzene with high yield and selectivity using silicic acid ester modified AZ-type zeolite such as Al-AZ, B-AZ, Cr-AZ. The-process is described for conversion of monoalkyl benzene having an alkyl group containing 1-3 carbon atoms. U.S. Pat. No. 5,233,111 describes catalytic process for selective alkylation of aromatic hydrocarbons, with special reference to 1,1-biphenyl, diphenyl ether, naphthalene etc over de-aluminated mordenite zeolite. The patent also describes propylation of ethylbenzene using mordenite based catalyst.

Disproportionation of toluene (U.S. Pat. No. 5,367,099) and disproportionation of ethylbenzene (U.S. Pat. No. 5,382,737) is described over ex-situ selectivated zeolite catalyst. A selectivated and steamed zeolite is contacted with toluene or ethylbenzene accomplishing high para-selectivity of the product para-xylene or para-diethylbenzene under conversion conditions of temperature from ~100° C. to ~700° C., pressure from about 0.1 atmospheres to 200 atmospheres, and a WHSV (weight hourly space velocity) of from about 0.08 to about 200 $h^{-1}$, and a hydrogen to hydrocarbon mole ratio of from 0 to 100.

It is to be emphasised that any product must meet certain specification for the purpose of commercial application. In other words, the impurity profile of a product is equally important as that of purity of the product. In case of para-diethylbenzene, some of such specification as laid down for the purpose of application as desorbent in PAREX process of M/s UOP are Purity 95 wt % (min), $C_8$ aromatics <0.2 wt %, $C_9$ aromatics <0.4 wt %, $C_{10}$+heavy aromatics (other than diethyl benzene isomers), <0.5%, Nitrogen 1 ppm (max), Sulphur 1 ppm (max), Chloride 1 ppm (max), Carbonyl Number 1 ppm by weight (max), Bromine Index 20 (max), The trace amount of unsaturated hydrocarbons in aromatic hydrocarbons are measured by potentiometric titration of the sample with potassium bromide-potassium bromate solution and is reported as 'Bromine Index' of the sample in consideration. The 'Bromine Index' of a hydrocarbon is defined as the number of milligrams of bromine consumed by 100 grams of the hydrocarbon sample under given conditions. 'Bromine Index' is usually determined by following the American Standard Test Method No. D-1491, (D1491-78). The sample is dissolved in a special solvent (comprising glacial acetic acid, carbon tetrachloride, methanol, sulphuric acid and a solution of mercuric chloride in methanol), and is titrated with 0.02 N potassium bromide-potassium bromate mixture. End point is determined potentiometrically using a glass-platinum electrode pair.

The trace amount of carbonyl function (in-the range of 0.1 to 100 milligram per litre) present as ketone or aldehyde in $C_5$ to $C_{18}$ hydrocarbons or alcohols are measured by chemical analysis and are reported as 'Carbonyl Number' of the sample under consideration. The 'Carbonyl Number' (also called Carbonyl No), is defined as milligrams of carbonyl functional per litre of the sample using acetophenone as standard. 'Carbonyl Number' of 'Parex' desorbent (para-di-ethylbenzene) is determined by following the American Standard Test Method No E-411 and UOP Method No 624. The results are normally used as indication of oxygen exposure of the 'Parex' and 'Molex' feedstocks. The ketone and aldehyde (carbonyls) in the sample is extracted and reacted with an acidic, alcoholic 2,4-dinitrophenyl hydrazine to form a phenyl hydrazone. Alcoholic potassium hydroxide is added to stop the reaction and convert the yellow hydrazone to a pink compound, the intensity of which is proportional to the carbonyl concentration. The intensity of the colour is measured at 480 nm in a spectrophotometer and the carbonyl content of the sample is determined from a standard calibration awe from which the carbonyl number is determined.

U.S. Pat. No. 5,811,613 issued on Sep. 22, 1998 and assigned to the assignee herein describes an effective process for production of para-diethylbenzene using ethylbenzene, ethanol, and steam in the presence of a pore size controlled galloaluminosilicate zeolite catalyst. However, in commercial operation of this patent, it was observed that the final para-diethylbenzene product, recovered from reactor effluent (by separation of the reactant and heavier hydrocarbons by-products), contains some objectionable impurities, like unsaturated hydrocarbons, and carbonyl compounds. For example, the final para-diethylbenzene obtained from the operation of the process described in the said U.S. Pat. No. 5,811,613, has been found to have 'Bromine Index' in the range of 60-70 and 'Carbonyl Number' in the range of 30-40. Such product needs further purification steps like treatment with acids to get rid of unsaturated hydrocarbons, and treatment with suitable organic reducing agents to reduce the carbonyl compounds, in order to meet the specification of the product for commercial applications Such steps not only add to the cost of production of the product, but also cause a loss of the valuable finished product. In addition, in some cases it may produce waste streams which may not be environment friendly.

Enhancement of para-selectivity, (the fraction of para-isomer in a mixture of disubstituted aromatics), by treatment with organosilicon compound is usually referred to in the art as 'selectivation' by 'silanation'. The organosilicon compound is usually known as 'selectivating agent'. The method normally comprises contacting zeolite with organosilicon compound, separation/removal of solvent (if used), and calcination of zeolite to deposit silica or polymeric silica as a layer on the zeolite.

It is known in the art that the efficiency of silica deposition in order to enhance the selectivity of the zeolite depends on the nature or the kind or the type or the molecular structure of the selectivating agent, i.e. the organosilicon compound employed. The efficiency of silica deposition also depends on the temperature of silanation, the solvents or the carrier for the organosilicon compound, the method or procedure adopted for the selectivation. Pretreatment of the zeolite, i.e. treatment carried out before selectivating the zeolite has also been found to affect the final selectivity of the zeolite. Also post-treatment, i.e. treatment after selectivating the zeolite have also been described in the art to further improve the selectivity of the zeolite for particular hydrocarbon conversion processes.

Selectivation of zeolites by silanation can be carried out in vapour phase or liquid phase. Liquid phase silanation is also referred as 'ex-situ silanation', or 'ex-situ selectivation'. The zeolite is impregnated with an organosilicon compound dissolved or dispersed in a carrier or solvent followed by calcination of such treated zeolite in an oxygen containing atmosphere under conditions sufficient to remove organic material therefrom and deposit siliceous material on the zeolite. Such ex-situ silanation may result in deposition of at least 1% by weight of siliceous material on the catalyst or zeolite.

Examples of various patents, which teach ex-situ selectivation of zeolites to enhance para-selectivity are U.S. Pat. No. 3,698,157 (to Allen et. al.), U.S. Pat. No. 4,002,697 (to Chen), U.S. Pat. Nos. 4,127,616 and 4,402,867 (both to Rodewald). U.S. Pat. No. 3,698,157 (to Allen et al) describes improved chromatographic separation of $C_8$ aromatic mixture for the recovery of para-xylene therefrom using aluminosilicate zeolite H-ZSM-5 modified with octadecyltrichlorosilane. U.S. Pat. No. 4,002,697 (to Chen) describes preparation of catalyst for xylene manufacture by toluene methylation. Silica modified catalysts employed for the purpose were based on zeolites like ZSM-5, ZSM-11 or ZSM-21 of average crystal size of greater than 0.5. μ, having surface deactivated by reaction with compounds of nitrogen or silicon, i.e. phenyl carbazole or dimethyldichlorosilane, (which are sufficiently large as to be unable to penetrate pores of crystalline aluminosilicate) followed by calcination Pyridine was employed as a solvent for dimethyldichlorosilane. U.S. Pat. No. 4,127,616 (to Rodewald) describes catalysts suitable for alkylation of toluene with methanol or ethanol, and toluene disproportionation to obtain selectively the corresponding para-dialkyl benzene. The catalyst was prepared by deposition of large organosilicon compound e.g. polymeric phenylmethyl silicone or polymeric methylhydrogen silicone on crystalline aluminosilicate H-ZSM-5, followed by calcination. Silica modified zeolite catalysts have been described in U.S. Pat. No. 4,402,867 (to Rodewald), utilizing aqueous emulsion of methylhydrogen silicone. Such catalysts contain added amorphous silica within the interior of crystalline structure of zeolite. The organosilicon compound employed here is small enough to enter pores of the zeolite.

When ex-situ selectivation process is repeated more than once, the procedure is referred to as 'multiple selectivation' or 'multiple silanation'. In multiple selectivation, the zeolite is treated at least twice, generally from 2-6 times with a liquid medium containing the organosilicon compound(s). In multiple selectivation method, the zeolite is calcined after each impregnation of organosilicon compound. Examples of multiple silanation are found in U.S. Pat. No. 4,060,568 (to Rodewald), U.S. Pat. Nos. 4,283,306 and 4,449,989 (both to Herkes), U.S. Pat. No. 5,349,114. (to Lago et al), U.S. Pat. No. 5,495,059 (to Beck et al), U.S. Pat. No. 5,552,357 (to Lago et al), U.S. Pat. No. 5,574,199 (to Beck et al.), U.S. Pat. Nos. 5,726,114 and 5,990,365 (to Chang et al).

Modification of zeolites described in U.S. Pat. No. 4,060,568 (to Rodewald), comprises preparing crystalline aluminosilicate zeolite catalyst containing amorphous silica within the interior crystalline structure of ZSM-5, by exposing zeolite to volatile silane of small molecular dimension, which preferably enters the pores of zeolites, followed by treatment with aqueous ammonia and calcination The patent describes a catalyst modified by three such treatments with intermediate calcination after each treatment, but provides no description of any enhancement in catalytic selectivity or activity over that which might follow from a single such treatment.

U.S. Pat. No. 4,283,306 and U.S. Pat. No. 4,449,989 (both to Herkes) also describe methods of modifying crystalline silica catalyst by application of such silica sources as tetraethylorthosilicate (TEOS), or phenyl methyl silicone. Interestingly, performance of the catalyst treated once with a TEOS solution followed by calcination, was better than that of )catalyst treated twice with TEOS, and calcined after each treatment, thus showing that twice treated catalyst is less active and less selective than once treated catalyst as measured by methylation of toluene by methanol. This indicates that multiple ex-situ silanation confers no advantage over single silanation, rather results in adverse effect on para-dialkylbenzene selectivity. U.S. Pat. No. 5,349,113 (to Chang et al) describes modification of molecular sieve catalyst by treating with substantially aqueous solution of a water soluble organosilicon compound. The method includes concurrent preselectivation and activation to get activated catalyst. The invention also comprises in-situ selectivation by passing a high efficiency para-xylene selectivating agent along with the reactants. U.S. Pat. No. 5,349,114 (to Lago et al) describes shape-selective hydrocarbon conversion over modified catalytic molecular sieve, which has been modified by (i) being preselectivated with a first silicon containing compound and (ii) subsequently steamed at about 280° C. to 400° C. The, patent indicates that the molecular sieve is modified in as-synthesized conditions. U.S. Pat. No. 5,495,059 (to Beck et al) also describes multiple ex-situ selectivation sequence employing an aqueous carrier for the organosilane compound. Each sequence includes an impregnation of the molecular sieve with the selectivating agent and a subsequent calcination of the impregnated molecular sieve. Selectivation of molecular sieves has been described during extrusion by agglomerating with organosilicon compound by Chang et al in U.S. Pat. No. 5,541,146. U.S. Pat. No. 5,552,357 (to Lago et al) describes catalyst modification by treatment of ZSM-5 in as-synthesised or in ion-exchanged form, first by treatment with a silicon containing polymer (propylamine silane polymer) in substantially aqueous solution, followed by calcination The catalyst was further in-situ selectivated with a second silicon containing compound. For multiple ex-situ selectivation during first stage, i.e. during treatment with propylamine silane polymer, the catalyst was calcined after first treatment and before the second treatment.

Post-treatment of selectivated zeolite with a dealuminizing agent, e.g. monovalent or polyvalent acids, triethylene diamine, urea, ethylenediamine tetra acetic acid, ammonium hexafluorosilicate is described in U.S. Pat. No. 5,567,666 (to Beck et al). U.S. Pat. No. 5,574,199 (to Beck et al) describes shape-selective aromatization with a catalytic molecular sieve, which has been modified by multiple ex-situ selectivation method. The method involves exposing the catalytic molecular sieve to at least two selectivation sequences, each sequence comprising contacting the catalyst with dimethylphenylmethyl polysiloxane in a solvent, followed by calcination. U.S. Pat. No. 5,726,114 (to Chang et al.) describes a method for modifying intermediate pore catalytic molecular sieve by multiple ex-situ selectivation process by contacting the zeolite with an aqueous emulsion comprising of a silicon-containing selectivating agent stabilized with the aid of surfactant and calcining the contacted molecular sieve after each impregnation of silica. The method further comprises of mild steaming of the silica deposited zeolite and also in-situ trim selectivation of the ex-situ selectivated zeolite. U.S. Pat. No. 5,990,365 describes a method for preparation of a catalyst comprising ZSM-5, rhenium and a selectivating agent, e.g. either coke or siliceous material or a combination thereof. The multiple selectivation is carried out by (i) combining a bound form of zeolite with an organosilicon compound (ii) calcining the organosilicon containing material to remove organic material therefrom to deposit siliceous material on the bound ZSM-5 and (iii) repeating steps (i) and (ii) at least once.

While the above mentioned art is of interest, there is no suggestion of enhancing the selectivity of metallosilicate by treatment with aqueous water after the zeolite has been contacted with organosilicon compound and before calcination of the zeolite to improve the silanation efficiency. There is also no suggestion in any of the prior art known to the applicants, of multiple silanation of metallosilicates without any intermediate calcination of organosilicon compound treated zeolite after each silanation. Additionally, there is no suggestion of recycling the solvents/carriers for multiple silanation.

In addition, the aforementioned art has always been directed towards improvement of para-isomer selectivity of the products. There has been no suggestion for providing a catalyst composite possessing concurrently reactant, product and transition state selectivity for a given process.

Therefore, it would be a significant advance and improvement in the art to overcome the difficulties, disadvantages and deficiencies associated with conventional methods and procedures for modifying catalytic metallosilicates, molecular sieves modified by such methods and the process of shape selective hydrocarbon conversion using such modified catalytic molecular sieves

OBJECTS OF THE INVENTION

Thus present invention also seeks to solve the difficulties, disadvantages, and deficiencies faced by the prior art by providing an improved method for modifying catalytic metallosilicate molecular sieves, and improved processes for shape selective hydrocarbon conversions, such as selective production of para-diethylbenzene through ethylation or disproportionation of a $C_8$ aromatics stream, (said aromatics stream being a by-product of naphtha cracker unit), meeting all the specifications required for commercial applications.

It is yet another object of the present invention to provide a catalyst composite capable of exhibiting contemporaneously all forms of selectivity viz, reactant selectivity, product selectivity as well as transition state selectivity.

It is an object of the invention to provide a complete, continuous and integrated process for the production of para-diethylbenzene (PDEB), using a low value C8 aromatics stream (called mixed xylene solvent or 'MXS' or py gas xylenes), obtained from pyrolysis gasoline or pygas aromatic stream), which is a by-product of naphtha cracking unit Another objective of the present invention is to provide a process for production of para-diethylbenzene, wherein the product meets all the specification for commercial application (as desorbent for adsorptive separation of para-xylene from a mixture of other $C_8$ aromatics) as well as for production of terephthalic acid by oxidation.

Another object is to provide an improvement on a process for production of para-diethylbenzene described in U.S. Pat. No. 5,811,613 assigned to assignee herein.

Another object is to provide a process for production of para-diethyl benzene using selectivated metallosilicate composite catalyst described in copending U.S. patent application Ser. No 09/935,991, filed on 23 Aug. 2001 and Ser. No. 10/319,307 filed on 14 Dec. 2002.

These and other objectives of the invention will be more apparent with the description of embodiments given hereinafter.

SUMMARY OF THE INVENTION

Accordingly, the present invention provides a complete integrated process for producing para diethylbenzene, employing a hydrocarbon :stream rich in ethyl benzene, obtained from pyrolysis gasoline or pygas stream. Such hydrocarbon streams are obtained from the naphtha cracker unit in a petrochemicals complex. More specifically the present invention relates to a process for production of para-diethylbenzene using a reactant stream rich in ethylbenzene, such as a $C_8$ aromatic stream, (mixed xylene stream or pygas xylenes stream from pyrolysis gasoline or pygas aromatic stream). Thus the present invention provides a process for production of para-diethylbenzene, which employs a novel low value $C_8$ aromatics stream, comprising of mainly ethylbenzene and xylene isomers along with small amounts of $C_7$, $C_9$ and $C_{10}$ aromatics compounds. The process comprises of contacting the reactant stream ($C_8$ aromatics stream containing ethylbenzene and xylenes from pyrolysis gasoline or pygas aromatic stream) and an alkylating agent such as ethylene, ethanol in the presence of a selectivated metallosilicate composite catalyst under specified conditions of operations, recovering the para-diethylbenzene and heavier hydrocarbon from reactor effluent by any known manner, suitably treating the recovered para-diethylbenzene and $C_{10}$+ aromatics product stream with clay material under specified conditions of operation to remove olefinic impurities, and finally recovering pure para-diethylbenzene product from the clay treated effluent by any known manner.

BRIEF DESCRIPTION OF THE ACCOMPANYING DRAWINGS

FIG. 1. Brief schematic of source of feedstock for para-diethylbenzene manufacture.

Figure 2:
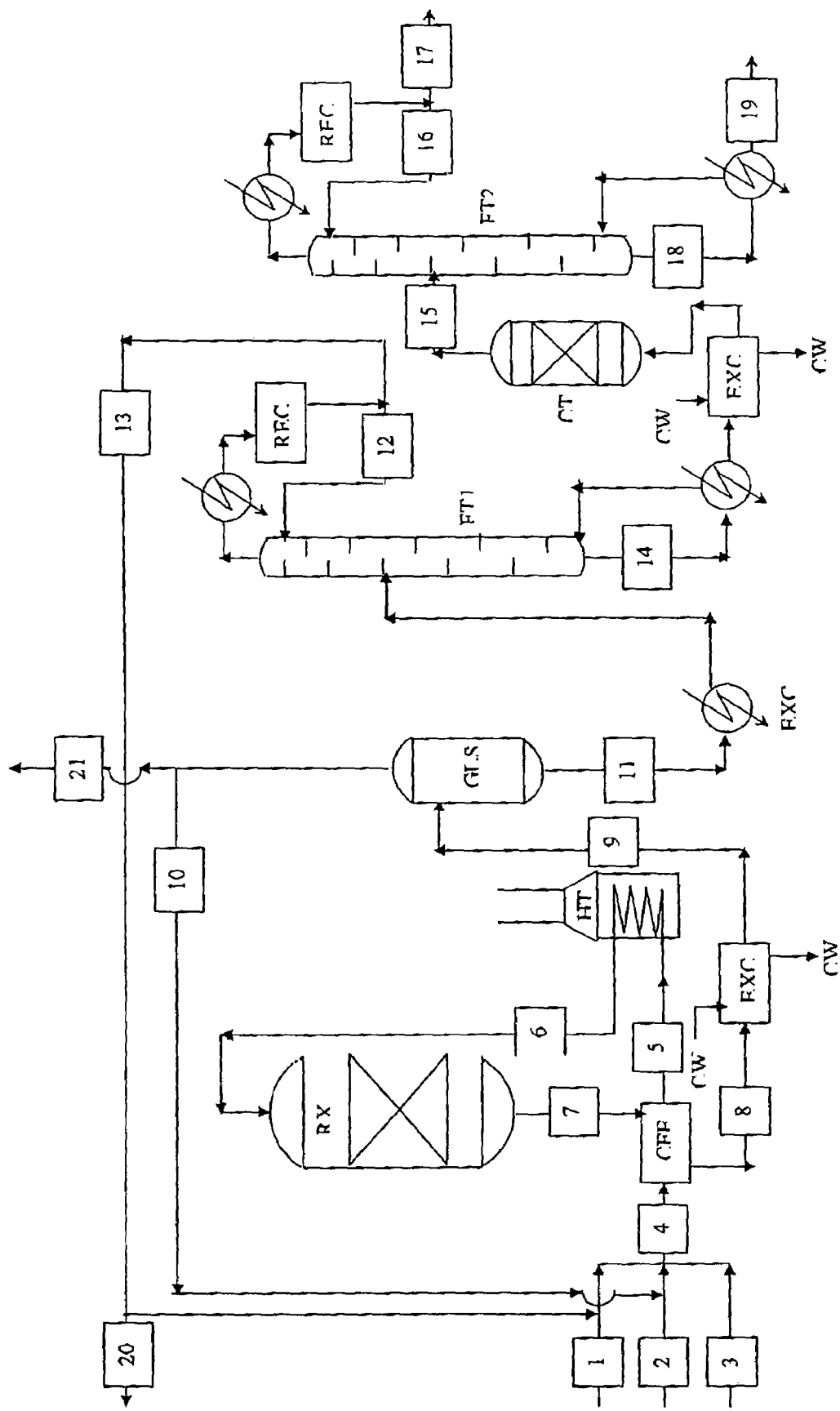

FIG. 2. Schematic flow diagram for the production of para-diethylbenzene

DETAILED DESCRIPTION OF THE INVENTION

In the present invention, para-diethylbenzene can be produced with a very high selectivity, by ethylation of a commercially readily available and cheap hydrocarbon stream such as US or pygas xylenes with ethylene or ethanol with a very high selectivity for para-diethylbenzene; The selectivity for para-diethylbenzene (among the diethyl benzene isomers) is usually 99% and frequently it is >99.3%. The invention also encompasses production of para-diethylbenzene through disproportionation of the said $C_8$ aromatic stream containing ethylbenzene and xylene isomer. In addition, according to the teaching of the present invention, the para-diethylbenzene product is suitable for commercial purpose as the product meets all the specifications for use as desorbent in the adsorptive separation of para-xylene from $C_8$ aromatic raffinate.

Thus the process of the invention comprises contacting a $C_8$ aromatics stream (containing mainly ethylbenzene and xylene) optionally with an ethylating agent, under specified conversion conditions, in presence of a selectivated metallosilicate catalyst composite, recovering the $C_{10}$ aromatics and heavier hydrocarbons containing mainly para-diethylbenzene by any known manner such as distillation, treating this recovered stream with a clay under specified operating conditions, finally recovering para-diethylbenzene from the treated stream by any known manner. In a preferred embodiment the present process for producing para-diethylbenzene comprises to yield para-diethylbenzene, which meets all the specification for use as a desorbent or for production of terephthalic acid. The embodiment extends and covers ethylation or disproportionation of ethylbenzene present in a "mixed xylene solvent" (MXS) stream or pygas xylenes streams wherein such streams are by-product of naphtha cracking unit and such stream are primarily mixture of ethylbenzene and xylenes along with some amounts of toluene, $C_9$ and $C_{10}$ or heavier aromatic compounds. The "mixed xylenes solvent" may also contain a small amount of non-aromatics or lighters compounds. Ethylation or disproportionation of such streams to produce para-diethyl benzene is effected by contacting the $C_8$ aromatics stream along with ethylene (or without ethylene, as the case may be), in the presence of a selectivated metallosilicate catalyst. Such ethylation or disproportionation of the said aromatics stream is effected at a temperature between 240° C. to 700° C., at a pressure between 0.1 to 200 atmospheres, and a weight hourly space velocity from about 0.1 to about 50 per hour. The molar ratio of $C_8$ aromatics to ethylene may be between 1:0 to 40:1. Hydrogen may be employed as a carrier gas and the molar ratio of hydrogen to hydrocarbon may be between 0:1 to 60:1.

The present invention also provides a catalytic hydrocarbon conversion process wherein simultaneous and contemporaneous existence of reactant selectivity, product selectivity as well as transition state selectivity is discovered. To explain firer, it is only the ethyl benzene present in the $C_8$ fraction of "Mixed Xylenes Solvent" feed stock which enters the pores of the modified metallosilicate catalyst described hereinbefore and herein after, reacts with the specified alkylating agent (or undergo disproportionation), and para-diethyl benzene produced within the channels of the modified metallosilicate catalyst, exits with extremely high selectivity. Although para-xylene present in the MXS feed stock can have ingress to the channels of the modified metallosilicate catalyst, however because of the space constraints within the interior of the channels of the catalyst, can not undergo any sort of conversion and comes out intact. Thus out of all the components present in the feed stock, only the ethyl benzene undergoes desired conversion, while all the other components remains substantially unaffected during the course of the reaction or the hydrocarbon conversion process, showing a high level of reactant selectivity. On the other hand, the ethyl benzene undergoes ethylation or disproportionation within the channels of the metallosilicate producing diethylbenzenes in thermodynamic equilibrium, but it is only the para-isomer, which can diffuse out quickly out of the channels and exit through the pores of the modified metallosilicate catalyst, showing an extremely high product selectivity. The other component which can enter the channels of the modified metallosilicate is para-xylene, but it remains unaffected and does not undergo any conversion because of space limitation within the channels of the catalyst, showing transition state selectivity.

Such a phenomenon of concurrent, simultaneous and combined selectivity for the preferred reactant, desired product, and inhibition of the unwanted reaction through non-compatible transition state, has not been reported or known hitherto in the art. More over the contemporaneous reactant, product and transition state selectivity has been embedded in a single modified metallosilicate catalyst.

In one aspect, the present invention includes a method for preparing a modified metallosilicate molecular sieve catalyst composite, useful for hydrocarbon conversion to produce para-dialkylbenzene and the said method comprising steps of
a) contacting an intermediate pore metallosilicate with an organosilicon compound in a solvent for a specific duration and then removing solvent.
b) combining or treating the organosilicon compound containing metallosilicate with water, water vapour, or water vapour containing atmosphere and then drying the product.
c) repeating the steps a) and b) any number of times for multiple silanation
d) calcining the product so obtained in an oxygen containing atmosphere under conditions sufficient to remove the organic material to obtain said modified metallosilicate molecular sieve catalyst composite.

wherein, in the said process calcining step is not repeated after each of step (a) and (b).

Ideally, in this embodiment, the organosilicon compound employed is water insoluble.

The catalyst prepared according to the above method provides better results for shape selective hydrocarbon conversion. In another embodiment of the invention, the organosilane employed is water soluble, and therefore, step (b), i.e., combining with water can be dispensed with.

Accordingly, the present invention also provides a method for preparing a modified metallosilicate molecular sieve catalyst composite, useful for hydrocarbon conversion to produce para-dialkylbenzene and the said method-comprising steps of
a) contacting an intermediate pore metallosilicate with a water soluble organosilicon compound in a solvent for a specific duration and then removing solvent.
b) drying the product so obtained.
c) repeating the steps a) and b) any number of times for multiple silanation
d) calcining the product so obtained in an oxygen containing atmosphere under conditions sufficient to remove the organic material.

wherein, in the said process calcining step is not repeated after each of step (a) and (b).

The present invention relates to a process for selective production of para-diethylbenzene from a mixed aromatic feedstock containing ethylbenzene and at least one other aromatic compound. The other aromatic compound may be benzene, mono-or di- or tri- or tetra-substituted alkyl benzene having alkyl group with carbon number 1 to 4 or a mixture thereof, along with small quantities of $C_1$ to $C_{10}$ hydrocarbons (saturated, unsaturated, linear, branched, acyclic, alicyclic in nature). Preferably the feedstock contains mainly ethylbenzene and mixture of xylene isomers along with some $C_7$ and $C_9+$ aromatic hydrocarbons and a small amount of $C_1$ to $C_{10}$ other hydrocarbons. Such feedstock is usually obtained as a by-product from pyrolysis gasoline or pygas stream, of naphtha cracking unit.

Referring to FIG. 1, at downstream of a naphtha cracker, the effluent stream containing hydrogen, methane, $C_2$ fraction, $C_3$ fraction, $C_4$ fraction, pyrolysis gasoline and $C_9$ are separated into different fractions. Pyrolysis gasoline or pygas stream is hydrogenated and the hydrogenated gasoline stream is sent to extraction unit to separate aromatics and non-aromatics. The said aromatic stream (separated in the extraction unit), is further fractionated to recover benzene, and toluene as overhead stream. The by-product of this stream is left out with $C_8$ aromatics along with some heavies such as $C_9$ aromatics or higher aromatics. Such by-products are called mixed xylenes streams (MXS) or pygas xylenes. Such a stream of $C_8$ aromatics contains mainly ethylbenzene and xylenes and some $C_9+$ aromatics or aromatics with 9 or more carbon atoms, and other $C_1$ to $C_{10}$ hydrocarbons in small quantities. Ethylbenzene content in this stream varies from about 30% to about 95% depending on the quality or nature of naphtha feedstock and the severity of the operation of the cracking unit as well as other upstream units. Usually the ethylbenzene in the mixed xylene solvent stream is in the range of 35%-95% and typically in the range of about 40% to about 90%.

The xylene content in the mixed xylene stream may vary in the range of about 5%-70%, depending on the quality of naphtha and the operating conditions of the cracker as well as other upstream units. Usually the xylene content in the mixed xylene solvent stream is in the range of about 15% to about 40% and typically in the range of about 20% to about 35%.

Since the distribution of isomers in these xylenes are in thermodynamic equilibrium, hence the para-xylene content is in the range of only about 3% to 10%. In addition the presence of large amount of other hydrocarbons such as ethylbenzene and meta xylene, renders it uneconomical for recovery of para-xylene from these streams. Thus normally it is disposed of as a solvent for use in the paint and agrochemical industry, at a very low price. With the invention of newer ecofriendly solvents for paint and agrochemical industry, the market for mixed xylene solvent is bound to decrease, and it is imperative to find better value-added application of such seams. On the other hand, para-diethylbenzene is a product the demand for which is bound to increase with increase in more and more capacity coming up for para-xylene production. However it is to be mentioned that the invention is not limited to the present feedstock, but can be practiced with any feedstock having similar nature and composition sourced from anywhere else, such as reformat from the naphtha reformer etc.

The present invention for production of para-diethylbenzene using such streams as described herein comprises of (a) alkylating the feed stock under conditions effective for alkylation, using an ethylating agent, over a selectivated metallosilicate composite catalyst and (b) recovering a product stream containing at least 95% para-diethylbenzene The ethylating agent may be selected from the group of ethylating agents such as ethylene, ethanol, diethyl ether, ethyl sulphate, ethyl chloride or a mixture thereof. Preferably the ethylating agent is ethylene. The ethylene may be of polymer grade or chemical grade.

The conditions for alkylation may vary depending on the feedstock and the ethylbenzene content therein as well as type of reactor such as fixed bed, fluidized bed, moving bed etc. For a fixed bed down flow reactor, the process can be operated at a temperature in the range of from about 240° C. to about 700° C., preferably in the range of about 260° C. to about 500° C. The reactor pressure may be in the range of about 0.1 atmospheres to about 200 atmospheres, preferably in the range of about 0.2 atmospheres to about 40 atmospheres. The feed rate as defined by weight hourly space velocity based on the weight hourly flow rate of hydrocarbon feed stream to the weight of the catalyst, may be in the range of about 0.1 per hour to 50 per hour, preferably in the range of about 0.5 per hour to 20 per hour. The molar ratio of the feedstock to the ethylating moiety (for example ethylene in ethylene or the ethyl group in ethyl chloride) in the said co-reactant stream (alkylating agent), is in the range of from about 50:1 to about 0.1:1, preferably in the range of about 30:1 to 0.1:1. It is also possible to operate the process without any alkylating agents as mentioned above. The process may be operated in the presence of a carrier gas selected from the group of nitrogen, hydrogen, steam or a combination thereof. The overall media should be substantially free from molecular oxygen or media containing molecular oxygen, said molecular oxygen including being both gaseous as well as dissolved form. A mixture of nitrogen and hydrogen may be used. Hydrogen or a mixture of nitrogen and hydrogen is particularly helpful in reducing the carbonyl number of the feedstock, particularly when the feedstock contains such impurities. The molar ratios of said carrier gas to said hydrocarbon stream containing ethylbenzene being in the range of about 0.05 to about 40, preferably in the range of 0.2 to 20. The process can be operated without any carrier gas also.

The process for the production of para-diethylbenzene comprised of contacting the aforementioned feedstock with ethylene under specified condition of conversion in the presence of a novel selectivated metallosilicate catalyst composite described hereinafter. The catalyst is preferably activated before process sets in. Such activation not only helps in prolonging the catalyst life but also its ability to remove carbonyl impurities present in feed stream. Such activation can be carried out in an atmosphere of hydrogen or a mixture of hydrogen and nitrogen, at a temperature in the range of at least 300° C. to about 600° C., preferably in the range of 400° C. to 550° C. for a period of 2 hour to 100 hours, preferably 4 hours to 50 hours. The operating pressure for carrying out such activation can be in the range of from 0.1 to 30 atmosphere although lower and higher pressure could also be employed, while the molar ratio of hydrogen to nitrogen may be in the range 100:1 to 1:100.

Referring to the FIG. 2, the feed stock along with the co-reactant (alkylating agent), is contacted under conversion conditions as described herein before, with a selectivated metallosilicate zeolite as described in copending U.S. patent application Ser. Nos. 09/935,991, filed on 23 Aug. 2001 and Ser. No. 10/319,307 filed on 14 Dec. 2002 of the present assignee.

The stream obtained immediately downstream of the reactor, namely the reactor effluent stream is separated into (a) a non-condensable light hydrocarbon stream rich in carrier gas content, which may be recyled back to the reactor, or used as a fuel gas, (b) a light liquid hydrocarbon fraction consisting of substantially aromatics and substituted aromatic compounds with a carbon number of up to and including 9, (c) an intermediate hydrocarbon stream consisting substantially of para-diethylbenzene along with hydrocarbons in the range of carbon numbers from $C_{10}$ to $C_{20}$ (or more) which upon further separation produces a product stream consisting of essentially pure para-diethyl benzene and another stream consisting of heavy hydrocarbon, of carbon number in the range 10 to 20, through suitable means such as distillation in a separation section. Any of the said hydrocarbon streams containing para-diethylbenzene subsequent to the separation of the said non-condensable stream, is treated with a suitable material such as clay. The clay may be selected from the group of bentonite, montmorillonite, attapulgite or any other available natural or modified clay. Commercially available clays such as, Tonsil clays grades 630, 630G, 616, 616G, 630GS, 616GS, Filtrol 54, Filtrol 24, APT-mx etc can also be used. The clay may be activated if required before using for such purpose. Such activation may be carried out in a stream of carrier gas, hydrogen, nitrogen or a mixture there of Preferably nitrogen may be used In the present invention, typical activation conditions are temperature in the range of about 20° C. to 300° C., pressure ranging from 0.01 vacuum to 50 atmospheres, earner gas flow rates gas hourly space velocities (GHSV) ranging from 1 to 5000 per hour. The clays are activated prior to use for bromine index mitigation of said streams; the said stream being the reactor effluent stream, or recovered product containing at least 95% para-diethylbenzene or the intermediate product stream containing about 88% to 95% para diethylbenzene and the balance $C_{10}$+heavy hydrocarbons.

The clay treatment operation may be done in a manner wherein the said stream, in liquid phase, is contacted with the said clay in a fixed bed reactor configuration with upward or downward flow, or a trickle bed downward flow operation, preferably in a fixed bed reactor configuration. The clay treatment may be carried out at a temperature in the range of from about 20° C. to about 300° C. The pressure during the clay treatment may be from about 1 atmospheres to 30 atmospheres. The liquid hourly space velocity may be from about 0.1 per hour to about 50 per hour. The effluent from the clay treater may require fractionation depending on the stream employed for removal of the olefinic impurities.

The final recovered product from the clay treater (and further fractionation if required) is substantially pure para-diethyl benzene with a purity of greater than 95 wt %, preferably greater than 99 wt %, bromine index less than 20, carbonyl number less than 1 wt ppm, Pt—Co color less than 10, sulfur, chloride and nitrogen each less than 1 wt ppm, suitable for commercial use including use as a desorbent in the separation of para-xylene from its isomers, using adsorbents such as used in the Parex process licensed by M/s Universal Oil Products (U.S.A). The para-diethylbenzene product thus obtained can also be used for production of terephthalic acid.

It is to be understood that treatment of hydrocarbons with clays to remove impurities such as olefins, are well known in the art, such as treatment of toluene or xylene streams with clays to remove olefinic impurities. Also other hydrocarbon streams, such as paraffinic hydrocarbons from superior kerosene during production of linear alkyl benzene, are treated with clay material to remove olefinic hydrocarbons. However, treatment of a substantially pure isomeric compound such as para-dialkylaromatics having alkyl group with more than one carbon, are hitherto not known in the art. The requirement involved herein is to ensure removal of the olefinic compounds without disturbing the isomer distribution of diethylbenzenes and without loss of para-diethylbenzene across the clay tower. The stream obtained after separation of non-condensable carrier gas rich hydrocarbons and the $C_6$-$C_9$ aromatics hydrocarbons compounds, and containing substantially para-diethylbenzene, heavy hydrocarbons of carbon number greater than or equal to 10 and small quantity of meta-diethylbenzene ortho-diethylbenzene is suitable for this application.

The present process of producing para-diethylbenzene is accomplished by contacting the said feedstock under the conversion conditions with a novel selectivated metallosilicate composite catalyst. The metallosilicates employed herein are of pentasil family, e.g. ZSM-5, ZSM-11 or isomorphous substituted derivatives thereof Preferred metallosilicates are Ga—Al-ZSM-5, Fe—Al-ZSM-5, Ga-ZSM-5, Fe-ZSM-5, Al-ZSM-5 and the like. The metallosilicate may be employed in the form as-synthesised, or calcined Na-form or ammonium form or in active H-form. Preferred is the H-form of the metallosilicate. The modified metallosilicate may be in unbound form or may be in a bound form with a binder. The binder may be silica, alumina, or silica alumina, clay, and the like or a mixture thereof. Preferred binders are silica, alumina, clay or a mixture thereof.

Preparation of modified galloaluminosilicate of pentasil family comprises (a) contacting galloaluminosilicate with an organosilicon compound in a solvent and separating the solvent; (b) optionally combining or treating organosilicon compound treated galloaluminosilicate with liquid water or water vapour or water vapour containing atmosphere and then drying the catalyst composite; (c) repeating steps (a) and (b) for multiple silanation; and (d) calcining the catalyst under conditions sufficient to remove organic material and deposit siliceous material on external surface of galloaluminosilicate, wherein in the said process calcining step is not repeated after each of steps (a) and (b).

The organosilicon compound may be either a silicone or a silane or a mixture thereof. Examples of organosilicon compounds include phenylmethyl silicone, tetraethoxy silane, 3-aminopropyltriethyoxy silane etc. When a silane is chosen as a selectivating agent, the preferred silanes are alkoxy silanes e.g. tetraethoxy silane, or 3-aminopropyl triethoxy silane. It is also preferred that the kinetic diameter of the selected organosilicon compound is larger than the pore size opening of the metallosilicate which is subjected to modification The solvent in which the organosilicon compound is dissolved may he any hydrocarbon liquid, e.g. aliphatic, alicyclic or aromatic hydrocarbons, e.g. $C_5$-$C_8$ hydrocarbons, like pentane, hexane, heptane, octane, cyclopentane, cyclohexane, cycloheptane etc., and benzene, toluene, xylene, or alcohols like, methanol, ethanol etc., or mixture thereof. A preferred solvent is low boiling in nature as well as non-polar and aprotic one. Water may also be employed when the organosilicon compound is soluble in it. Preferred solvents are cyclohexane, toluene, mixture of toluene and methanol, water etc.

The concentration of the organosilicon compound in the solvent may be in the range of greater than 1 weight percent to less than 99 weight percent, preferably greater than 2% to less than 50%, more preferably, 5% to 25%. The organosilicon compound containing solution is combined with the metallosilicate and treated at a temperature from 0° C. to the boiling point of the solvent for duration of 0.1 to 24 hours. It may be preferable to soak the metallosilicate in the selectivating solution, i.e. the organosilicon compound containing solution for about 1 hour to 16 hours, or to reflux the combination of metallosilicate and the selectivating agent containing solution for about 0.5 hour to about 12 hours. Subsequently, the solvent is separated by any known means, e.g. by decantation, by filtration or by distillation or by simply allowing for air drying at room temperature and pressure. However, when an organic solvent is employed, it has been found convenient to separate the metallosilicate from the solution by either filtration or distillation. It is preferred to separate the metallosilicate by distillation because such a procedure leaves the metallosilicate substantially free from the organic solvent. In the case of other solvents like water etc, the metallosilicate may be recovered by decantation or filtration.

In an embodiment of the present invention, the solvent employed for dissolving the organosilicon compound is recycled from batch to batch For example, the solvent employed for silanation of one batch of metallosilicate catalyst is recovered and reused for the silanation of second batch of metallosilicate and so on. Such a procedure has the advantage of minimum the liquid effluent to zero level in a commercial unit producing such catalyst.

In another embodiment of the present invention, the metallosilicate is treated with liquid water subsequent to treatment of the metallosilicate with organosilicon compound. The procedure for the treatment may be like addition of the metallosilicate to water or vice-versa However, it is preferable and convenient to add water to the organosilicon compound containing metallosilicate. The amount of water added may be in the range of from 1 to 200 percent, preferably, 2% to 100% of the mass of the metallosilicate, more preferably from 5% to 90% of the mass of metallosilicate, and most preferably, the volume of water added may be somewhat approximately equal to the interparticle volume of mass of the metallosilicate. The wet extrudates are then dried at a temperature of 10 to 150° C., preferably, 50° C.-150° C. for 1-24 hours, more preferably, at a temperature of 80° C.-130° C. for 2-20 hours. Alternatively, organosilicon compound containing catalyst composite extrudates may be dried in water vapour containing atmosphere at a temperature of 80° C.-130° C. for 2-20 hours.

It is believed that alkoxysilanes, such as tetraethoxysilane or 3-aminopropyltriethoxy silane which have larger kinetic diameter than the pore openings of pentasil metallosilicates, cannot enter into the channels, and hence react only with acidic centres which are located on the external surface of the metallosilicates. In a first step, the alkoxysilane molecule gets adsorbed and/or anchored on the external surface acidic sites. In a second step, the reaction between the adsorbed alkoxysilane and the anchored alkoxysilane or between the anchored alkoxysilane molecules takes place leaving out either dimethyl ether or ethyl alcohol. The reaction may be considered as a sort of polymerization accompanied by hydrolysis. While not wishing to be limited by theory, it is believed that the addition of water facilitates the hydrolysis of the anchored alkoxysilane on the external surface of the metallosilicate. This increases efficiency of deposition of layered siliceous material, when the organosilicon compound containing metallosilicates are calcined for the above said purpose.

If a second selectivation, i.e. multiple silanation is not targeted, the catalyst extrudates are then calcined in an oxygen containing atmosphere, e.g. air, oxygen, or a mixture of nitrogen and oxygen etc. The temperature of calcination may be in the range of 160° C. to 800° C., preferably in the range of 300 to 600° C. and most preferably, at 400° C. to 550° C. The calcination is done at atmospheric pressure for 2 to 20 hours, preferably 4 to 12 hours. The gas hourly space velocity of the oxygen containing gas or air is in the range of 1 to 5000 $h^{-1}$.

According to a preferred embodiment of the present invention, the multiple selectivation, i.e. the multiple treatments with the organosilicon compound, are carried out without going for calcination after each selectivation. For example, the second treatment with the organosilicon compound (the selectivating agent) is carried out by repeating the procedures of steps (a), and (b) as described above. The third treatment with the organosilicon compound is carried out by repeating step (a), (b) above after second treatment. Thus, inventive process of modifying metallosilicate using multiple selectivation scheme as described hereinabove, avoids calcination after each selectivation and can be termed as "Repeated Soak and Dry" (RSD) selectivation method.

Such a process from the commercial point of view, is more energy efficient than that of the conventional procedure for modification, of zeolites through multiple silanation, wherein the zeolite is calcined after each treatment with the selectivating agent (i.e. the organosilicon compound). In addition, the emissions released during calcinations are also reduced since the intermediate calcination steps themselves have been dispensed with.

While wishing not to be limited by any theory, it will be appreciated by those skilled in the art that repeated calcination of metallosilicates at high temperatures viz. at greater than 500° C. for a long duration may be associated with some loss of acid sites of metallosilicates, including the acid sites located at the external surface. Therefore, the multiple silanation on such surfaces of metallosilicates might be less efficient, as compared to those where such loss of acid sites has not taken place. Thus, the present method of multiple silanation without any intermediate calcination step has an added advantage over the conventional procedure.

In another embodiment of the present invention envisaging multiple treatment with organosilicon compound (i.e. the selectivating agent), the organic solvent is recycled from the first treatment with selectivating agent For example, during the second treatment with organosilicon compound, the solvent recovered from the first treatment is employed. Thus, there is no final liquid effluent in the whole method of preparation of the modified metallosilicate catalyst composite.

Subsequent to the multiple selectivation of the metallosilicate (according to the RSD selectivation method), the catalyst is finally calcined in an oxygen containing atmosphere, e.g. air, oxygen, a mixture of nitrogen and oxygen. The temperature of calcination may be in the range of 150° C. to 800° C., preferably, in the range of about 300° C. to 600° C. and most preferably, at about 400° C. to 550° C. The duration of calcination may be in the range of 2 to 10 hours preferably, 3 to 8 hours, at atmospheric pressure. The gas hourly space velocity of the oxygen containing gas or air may in the range of 1 to 5000 $h^{-1}$.

The present invention also provides a process for shape-selective hydrocarbon conversion, using the modified metallosilicate composite, as described herein above. Such shape-selective reactions include disproportionation or alkylation of mono alkyl benzene to selectively produce para-dialkylbenzene, i.e. disproportionation of toluene to benzene and a mixture of xylenes containing mostly para-xylene. Similarly, ethylbenzene may be disproportionated over the catalyst of present invention to benzene and selectively para-diethylbenzene. Ethylbenzene can be ethylated using ethylene or ethanol to para-diethylbenzene employing the catalyst of the present invention. Toluene can be alkylated with methanol or ethylene or ethanol towards selective formation of para-xylene or para-ethyl toluene. The present catalyst can also be employed for selective de-ethylation of ethylbenzene (i.e. converting ethylbenzene to benzene and ethylene) from a mixture of $C_8$ aromatics containing ethylbenzene and xylene.

As per process conditions described in U.S. Pat. No. 5,811,613 (to Bhat Das and Halgeri), the entire content of which is incorporated herein by reference, the present catalyst may be employed for catalyzing vapour phase ethylation of ethylbenzene with ethanol to produce para-diethylbenzene, at a temperature of 300° C. to 500° C., weight hourly space velocity 0.01 to 10 $h^{-1}$, in the absence of any carrier gas and using steam as co-feed.

As per the process conditions described in European Patent EP 0369078 the entire content of which is incorporated herein by reference, the present catalyst may be employed for conversion of $C_8$ aromatic conversion, particularly for de-ethylation of ethylbenzene. The present catalyst may also be employed along with the conventional $C_8$ aromatic isomerization catalyst for improved performance in terms of selective and enhanced ethylbenzene conversion of the isomerization feed.

The catalyst of the present invention, prepared by the RSD selectivation method described herein above is particularly useful for selective ethylation of $C_8$ aromatics containing ethylbenzene and xylenes, or mixed xylene stream or pygas xylene stream The invention will now be described in greater detail with the reference to the following examples, which are presented here for the purpose of illustration only and should not be construed as limitative of the scope of the present invention.

EXAMPLE 1

Catalyst A (Comparative): 100 gm. of H—Ga—Al-ZSM-5 extrudates were soaked in a solution containing 32.5 gm tetraethoxy silane in a mixture of 100 ml toluene and 60 ml methanol for 6 hours at room temperature and pressure. The solvents (toluene and methanol) were distilled off and the extrudates were dried in oven at 120° C. overnight. Finally, the tetraethoxy silane treated extrudates were calcined in a flow of air at 535° C. for 8 hours.

Catalyst B: This example shows the effect of addition of liquid water in selectivation procedure. 100 gm of Ga—Al-ZSM-5 extrudates in H-form were added to a solution of 32.5 gm of tetraethoxy-silane in solvent mixture of 100 ml toluene and 60 ml methanol at ambient conditions and allowed to soak for 6 hours. The extrudates were recovered by distilling off the solvents. 50 ml of water was added to the extrudates and left for 30 minutes. The wet extrudates were then dried at 120° C. for 12 hours, and calcined at 540° C. in air for 8 hours.

Catalyst C: This example shows the effect of presence of water vapour in selectivation procedure. 100 gm of Ga—Al-ZSM-5 extrudates in H-form were added to a solution of 32.5 gm of tetraethoxy silane in solvent mixture of 100 ml toluene and 60 ml methanol at ambient conditions and allowed to soak for 6 hours. The extrudates were recovered by distilling off the solvents. The extrudates were then dried at 120° C., in an oven fill of moisture, for 12 hours. This was achieved by putting a water filled beaker in the oven where the extrudates were dried. Amount of water is two times that required for complete hydrolysis of anchored organosilicon compound. The dried extrudates were calcined at 540° C. in air for 8 hours.

The performance of the catalysts above (Catalyst A, B and C) were evaluated for producing para-diethylbenzene using ethylbenzene and ethanol as reactant. The reactor was continuous fixed bed down flow, integral reactor. Feed stream containing ethylbenzene and ethanol were preheated and put through the reactor using hydrogen carrier gas. The products were condensed, collected and analysed by Gas Chromatograph using capillary column. Reaction conditions and the results are described in Table-1.

TABLE 1

Performance of selectivated metallosilicates for para-diethylbenzene production.

|  | Catalyst A | Catalyst B | Catalyst C |
|---|---|---|---|
| Lighters | 0.05 | 0.05 | 0.05 |
| Benzene | 2.73 | 3.0 | 2.42 |
| Toluene | 0.19 | 0.23 | 0.17 |
| Ethyl Benzene | 81.90 | 81.62 | 83.42 |
| Xylenes | 0.16 | 0.20 | 0.16 |
| $C_9$ Aromatics | 0.34 | 0.34 | 0.26 |
| Meta-diethyl benzene | 3.45 | 3.00 | 2.41 |
| Para-diethyl benzene | 10.63 | 10.93 | 10.61 |
| Ortho-diethyl Benzene | 0.01 | 0.01 | <0.01 |
| $C_{10}$+ Aromatics | 0.54 | 0.62 | 0.50 |
| Total DEBs | 14.09 | 13.94 | 13.02 |
| PDEB Selectivity | 75.44 | 78.41 | 81.49 |

Temperature = 330° C.,
WHSV = 3/h,
Ethylbenzene:ethanol = 8:1 mol/mol
Hydrogen:Hydrocarbon = 2 mol/mol,
Pressure = ambient
DEBs = Total di-ethyl benzenes (meta- + para- + ortho- diethyl benzene)
PDEB = para-diethyl benzene
PDEB selectivity = (PDEB in product × 100)/total diethyl benzenes
Xylenes were in near thermodynamic equilibrium mixture of para-, meta- and ortho isomers.

EXAMPLE 2

Catalyst D; This example illustrates the improved multiple silanation method of modification with addition of liquid water. The example is given for two silanation, but the technique holds for any number of silanation. The two silanation were carried out by repeating the complete procedure as described in case of Catalyst B.

Catalyst E: This example illustrates the improved multiple silanation method of modification in the presence of water vapour. The example is given for two silanation, but the technique holds for any number of silanations. The two silanations were carried out by repeating the complete procedure as described in case of Catalyst C.

Catalyst F: This example illustrates multiple silanation without any calcination after each silanation The example is shown for two silanations but holds good for any number of silanations. 100 gm of Ga—Al-ZSM-5 extrudates in H-form were added to a solution of 32.5 gm of tetraethoxy silane in solvent mixture of 100 ml toluene and 60 ml methanol at ambient conditions and allowed to soak for 6 hours. The extrudates were recovered by distilling off the solvents. 50 ml of water was added to the extrudates and left for 30 minutes. The wet extrudates were then dried at 120° C. for 12 hours. Without going for calcination, the dried extrudates were subjected to a second silanation following the procedure just described. The extrudates were finally calcined at 540° C. in air for 8 hours. More examples of similar nature for preparation of catalyst are provided in copending U.S. patent application Ser. No. 09/935,991, filed on 23 Aug. 2001 of the present assignee.

Performance of the catalysts D, E, and F were evaluated and results are presented in table 2.

TABLE 2

Performance of selectivated metallosilicates for para-diethylbenzene production.

|  | Catalyst D | Catalyst E | Catalyst F |
|---|---|---|---|
| Lighters | 0.05 | 0.05 | 0.05 |
| Benzene | 2.65 | 2.36 | 2.32 |
| Toluene | 0.26 | 0.25 | 0.26 |
| Ethyl Benzene | 82.67 | 83.00 | 82.92 |
| Xylenes | 0.12 | 0.12 | 0.11 |
| $C_9$ Aromatics | 0.35 | 0.43 | 0.40 |
| Meta-diethyl benzene | 0.36 | 0.12 | 0.08 |
| Para-diethyl benzene | 12.94 | 13.46 | 13.53 |
| Ortho-diethyl Benzene | 0.01 | <0.01 | <0.01 |
| $C_{10}$+ Aromatics | 0.39 | 0.21 | 0.33 |
| Total DEBs | 13.31 | 13.58 | 13.61 |
| PDEB Selectivity | 97.2 | 99.11 | 99.41 |

Temperature = 330° C.,
WHSV = 3/h,
Ethylbenzene:ethanol = 8:1 mol/mol
Hydrogen:Hydrocarbon = 2 mol/mol,
Pressure = ambient

EXAMPLE 3

Catalyst F was tested for performance in a 'CATATEST' unit using 'MXS' (Mixed xylene solvent, or pygas xylene) and ethylene to check catalyst performance and selectivity for para-diethylbenzene as well as stability. The results are given in table 3.

TABLE 3

Catalytic performance of selectivated metallosilicates for para-diethylbenzene production, using mixed xylene solvent and ethylene.

| Liquid Product | | Time on Steam, hr. | | | | |
|---|---|---|---|---|---|---|
| Analysis, wt % | Feed | 40 | 95 | 180 | 260 | 380 |
| Lighters |  | 0.09 | 0.05 | 0.07 | 0.16 | 0.06 |
| Benzene |  | 1.1 | 1.16 | 0.84 | 0.81 | 0.79 |
| Toluene | 0.66 | 0.73 | 0.71 | 0.69 | 0.68 | 0.69 |
| Ethylbenzene | 75.28 | 66.3 | 66.52 | 66.28 | 66.57 | 67.01 |
| Xylenes | 23.15 | 22.69 | 22.68 | 22.77 | 22.75 | 22.61 |
| $C_9$ aromatics | 0.87 | 1.06 | 0.99 | 1.03 | 1.08 | 0.98 |
| Meta-diethylbenzene |  | 0.06 | 0.06 | 0.06 | 0.06 | 0.05 |
| Para-diethylbenzene |  | 7.56 | 7.4 | 7.82 | 7.42 | 7.4 |
| Ortho- diethylbenzene |  | <0.01 | <0.01 | <0.01 | <0.01 | <0.01 |
| $C_{10}$+ aromatics | 0.04 | 0.41 | 0.43 | 0.44 | 0.47 | 0.41 |

TABLE 3-continued

Catalytic performance of selectivated metallosilicates for para-diethylbenzene production, using mixed xylene solvent and ethylene.

| Liquid Product | | Time on Steam, hr. | | | | |
|---|---|---|---|---|---|---|
| Analysis, wt % | Feed | 40 | 95 | 180 | 260 | 380 |
| Total DEBs, wt % | | 7.62 | 7.46 | 7.88 | 7.48 | 7.45 |
| PDEB Selectivity, % | | 99.21 | 99.20 | 99.24 | 99.20 | 99.33 |

Temperature = 330° C.,
WHSV = 3/h,
Ethylbenzene (in MXS):ethylene = 8:1 mol/mol,
Pressure 2 bar (g),
Hydrogen:Hydrocarbon = 2 mol/mol

EXAMPLE 4

Catalyst F was tested for performance in a 'CATATEST' unit (Geomecanique, France), using 'MXS' (mixed xylene solvent, or pygas xylene) to check catalyst performance and selectivity for para-diethylbenzene as well as stability, through ethylbenzene disproportionation mode at various temperatures. The results are given in table 4.

TABLE 4

Catalytic performance of selectivated metallosilicates for para-diethylbenzene production, using mixed xylene solvent (and without using any ethylating agent).

| Liquid Product | | Temperature, ° C. | | | | |
|---|---|---|---|---|---|---|
| Analysis, wt % | Feed | 330 | 350 | 380 | 390 | 400 |
| Lighters | 0.01 | 0.06 | 0.05 | 0.13 | 0.28 | 0.43 |
| Benzene | 0.00 | 3.37 | 6.17 | 6.95 | 8.55 | 8.91 |
| Toluene | 0.62 | 0.86 | 1.05 | 0.88 | 1.07 | 1.24 |
| Ethylbenzene | 75.61 | 67.78 | 62.17 | 59.26 | 56.27 | 54.06 |
| Xylenes | 22.98 | 23.04 | 23.06 | 23.15 | 23.07 | 23.16 |
| $C_9$ aromatics | 0.75 | 0.39 | 0.58 | 0.60 | 0.79 | 1.02 |
| Meta-diethylbenzene | 0.00 | 0.02 | 0.05 | 0.06 | 0.08 | 0.10 |
| Para-diethylbenzene | 0.00 | 4.35 | 6.69 | 8.77 | 9.65 | 10.58 |
| Ortho-diethylbenzene | | <0.01 | <0.01 | <0.01 | <0.01 | <0.01 |
| $C_{10}+$ aromatics | 0.00 | 0.13 | 0.16 | 0.17 | 0.24 | 0.43 |
| Total DEBs, wt % | | 4.37 | 6.74 | 8.83 | 9.73 | 10.68 |
| PDEB Selectivity, % | | 99.46 | 99.24 | 99.28 | 99.18 | 99.06 |

WHSV = 3/h,
Pressure 7 bar (g),
Hydrogen:Hydrocarbon = 2 mol/mol.

EXAMPLE 5

The performance of the catalyst F was also tested with different types of feed containing varied amounts of ethylbenzene therein. Feed reaction conditions and results are summarized below in Table 5.

TABLE 5

Performance of selectivated metallosillcate composite catalyst for the process of producing PDEB using different feedstcok containing varying amount of ethylbenzene.

| | Liq. Analysis | | | | | | | | | | | |
|---|---|---|---|---|---|---|---|---|---|---|---|---|
| | Ar. Feed | Product | Ar. Feed | Product | Ar. Feed | Product | Ar. Feed | Product | Ar. Feed | Product | Ar. Feed | Product |
| Lighters | | | | | | | | | | | | |
| Benzene | 0.57 | 2.17 | 0.04 | 1.35 | 0.02 | 0.58 | 0.02 | 0.73 | 0.03 | 0.33 | 0.03 | 0.17 |
| Toluene | 0.05 | 0.17 | 0.67 | 0.82 | 0.98 | 0.76 | 1.16 | 1.12 | 1.22 | 1.03 | 1.14 | 1.12 |
| Naphthenes | | | | | 1.64 | 1.65 | 3.69 | 3.51 | 5.12 | 4.46 | 6.67 | 6.01 |
| Ethyl Benzene | 99.24 | 90.1 | 75.57 | 68.26 | 60.59 | 53.01 | 45.07 | 39.48 | 28.77 | 24.19 | 12.65 | 10.45 |
| Xylenes | 0.11 | 0.12 | 23.31 | 22.95 | 36.13 | 37.07 | 49.64 | 50.2 | 64.43 | 65.04 | 79.34 | 79.32 |
| C9 + Arom | | 0.12 | 0.41 | 0.52 | 0.28 | 0.53 | 0.21 | 0.28 | 0.16 | 0.38 | 0.04 | 0.29 |
| MDEB | | 0.07 | | 0.06 | | 0.06 | | 0.04 | | 0.04 | | <0.01 |
| PDEB | | 7.09 | | 6.02 | | 6.22 | | 4.33 | | 4.43 | | 2.55 |
| ODEB | | <0.01 | | <0.01 | | <0.01 | | <0.01 | | <0.01 | | <0.01 |
| C10 + Arom | 0.03 | 0.16 | 0.02 | 0.36 | 0.12 | 0.21 | 0.31 | 0.27 | 0.10 | 0.13 | 0.09 | |
| DEBYield, wt % | | 7.16 | | 6.08 | | 6.28 | | 4.37 | | 4.47 | | 2.55 |
| PDEB Selec., % | | 99.02 | | 99.01 | | 99.04 | | 99.08 | | 99.11 | | 100.00 |

Temp = 330° C.,
whsv = 3.5/h,
Aromatic hydrocarbon:Ethanol = 8:1 (mole/mole),
$H_2$/Hydrocarbon = 2 (mole/mole)
Ar. Feed = Aromatic Feed,
MDEB = meta-Diethyl benzene,
PDEB = para-diehtyl benzene,
ODEB = Ortho-diethyl benzene

EXAMPLE 6

This example is in reference with FIG. 2 which shows the process flow diagram for production of para-diethylbenzene using aromatic hydrocarbon stream described herein before and hereinafter. The notation used are given below;

CFE=Combined Feed Effluent Exchanger; HT=Heater, RX=Reactor; EXC=Heat Exchanger; CWS=Cooling water Supply; CWR=Cooling water Return; GLS=Gas Liquid Separator, FT1=Fractionation Tower1; REC=Overhead Receiver; CT=Clay Tower; FT2=Fractionation
Tower 2;

STREAMS: 1=Fresh MXS; 2=Fresh Hydrogen; 3=Fresh Ethylene; 4,5,6=Combined Feed; 7,8,9=Reactor Effluent; 10=Off-Gas Recycle to process; 11=Separator Liquid; 12 Reflux, 13 Un-reacted MXS recycle to process; 14=C10+ aromatics; 15 Clay treated C10+ Aromatics; 16 Reflux; 17=Pure PDEB Product; 18 & 19 Heavy aromatics; 20=Un-reacted MXS Drag Stream: 21=Off-Gas to Fuel gas/Flare In FIG. 2, Stream 1 is a reactant stream, typically a MXS (mixed xylene) stream also referred to as pygas xylene stream. The primary source of this stream is a Naphtha Cracker. Downstream of the naphtha cracker a stream consisting primarily of hydrocarbons with carbon numbers 6 to 8 is separated by distillation, catalytically hydrogenated in a hydrogenation section and then sent to an aromatics extraction section In the extraction section aromatic hydrocarbons with carbon numbers 6-8 are extracted by any suitable means such as sulfolane extraction. The recovered aromatics are then rendered free from sulfolane in a stripper section. This aromatic hydrocarbon stream, which is substantially free from sulfolane, is then sent to a fractionation section where benzene ($C_6$ aromatic) and toluene ($C_7$ aromatic) are removed overhead by distillation. The bottoms stream is a mixed xylene stream containing substantially ethylbenzene (30-85wt %) and xylenes (68-13wt %) along with small quantities of primarily aromatic hydrocarbons of carbon numbers 7 and 9 and trace quantities of hydrocarbons with carbon number greater than 9. Stream 2 is hydrogen, used as carrier gas. The source of hydrogen (without being limited to these) is by-product from a caustic soda unit or from downstream of a naphtha cracker unit or off-gas from either platforming unit or Reformer unit or a Paraffins dehydrogenation unit, or off-gas from a polyethylene unit, with or without a PSA (pressure Swing adsorption) unit at downstream for purification Stream 3 is a source of ethylene, which is the co-reactant (ethylating agent) in the process, and is from downstream of a naphtha cracker or gas cracker or a ethane dehydrogenation unit (without being limited to these), said ethylene could either be of polymer grade or chemical grade. Stream 4 is a combined feed stream consisting of a fixture of streams 1, 2 and 3 and could be in a mixed vapor liquid phase or vapor phase. Stream 4 is preferably heated up by exchanging heat with the reactor effluent in a combined feed effluent exchanger (CFE). Stream 5 is a partially heated combined reactant stream downstream of the CFE, which is further heated to process temperature in a heater (HT), which may be oil or gas fired or electrical heater. Stream 6 which is downstream of the heater (HT) is a fully vaporized combined reactant stream heated to process temperature and fed to reactor (RX) containing the catalyst used in the present process. Stream 7 is a reactor effluent stream in vapor form, which is cooled by exchange of heat with combined reactant feed in combined feed effluent exchanger (CFE). Stream 8 which is a partially cooled reactor effluent stream downstream of CFE is further cooled to temperatures in the range 30° C.-80° C. in a heat exchanger (EXC) using a suitable coolant such as cooling water. The cooled reactor effluent, stream 9, is then fed to a Ga-Liquid separator (GLS) where non-condensable off-gas (stream 10) is separated as an overhead stream. Part of this stream is recycled back to the process as stream 10 while a part is routed preferably to fuel gas header for use as fuel gas or to a flare header (stream 21). Stream 11 is a component of the reactor effluent, which is condensable under conditions in GLS. This stream is pre-heated in exchanger (EXC) and fed to I stage fractionation column (FT1). Stream 12 which is a reflux to FT1 from overhead receiver (REC) is un-reacted mixed xylene (MXS), consisting primarily of ethyl benzene and xylenes along with hydrocarbons of carbon numbers 6, 7, 9 and small quantities of hydrocarbons with carbon number greater than 9. Part of this stream may be withdrawn as stream 13, and directly recycled to process. Stream 20 is a part of stream 13, which is dragged intermittently (to outside the process loop) to contain build-up of concentrations of by-products as well as xylenes in the MXS feed to process. In an integrated petrochemical complex where fresh mixed xylene stream is continuously produced, the entire Stream 13 may be blended and reprocessed along with the C6-C8 aromatic extract stream in a fractionation section of aromatics extraction plant and then fed back to the reactor as 'fresh' feed, in which case there is no necessity for direct recycle of unreacted product from overhead of FT1 to process. Stream 14, which is withdrawn from bottom of FT1 consists primarily of the main product para-diethylbenzene small quantities of other isomers of di-ethylbenzene and heavy hydrocarbons of carbon number 10 and greater. This stream is passed-through a heat exchanger (EXC) and fed to a clay tower (CT) for removal of olefinic hydrocarbon impurities. Stream 15, which is downstream of clay treater is then fed to a second fractionation column (FT2) where pure para-diethylbenzene (PDEB) product is recovered as overhead stream. Stream 16 is reflux to FT2 from overhead receiver (REC) while stream 17 is withdrawal of pure PDEB. Stream 17 is substantially pure PDEB with a PDEB content greater than 95 wt % and preferably greater than 98 wt % and still more preferably greater than 99 wt %, balance other isomers of di-ethylbenzene, small quantities of aromatic hydrocarbons with carbon numbers 8 and 9 and heavy hydrocarbons, other than diethylbenzene, with carbon number 10 or greater. Streams 18 and 19 are heavy aromatics-consisting substantially of heavy hydrocarbons with carbon number 10 and higher along with small quantity of Para-diethylbenzene and other isomers of diethylbenzene. Stream 19 drawn from bottom is used as fuel or recycled to naphtha cracker as cracking feedstock.

The analyses and composition of various streams are incorporated in table 6 below.

Modifications and improvements are possible based on the above disclosure and are intended to fall within the scope of the invention described hereinbefore.

TABLE 6

Stream Composition Summary

| | \multicolumn{14}{c}{STREAM} | | | | | | | | | | | | | |
|---|---|---|---|---|---|---|---|---|---|---|---|---|---|
| | 1 | 2 | 3 | 4, 5, 6 | 7, 8, 9 | 10, 21 | 11 | 12, 13, 20 | 14 | 15 | 16, 17 | 18, 19 |
| Hydrogen | — | 99.95 (mole %) | — | 3.55 | 3.55 | 54.61 | — | — | — | — | — | — |
| Ethylene | — | — | 99.95 | 2.28 | 0.61 | 9.38 | — | — | — | — | — | — |
| C1, C3-C5 | — | — | — | — | 2.34 | 36.01 | — | — | — | — | — | — |
| Non-aromatics | <0.01 | — | — | <0.01 | 0.13 | — | 0.14 | 0.16 | — | — | — | — |
| Benzene | <0.01 | — | — | <0.01 | 0.84 | — | 0.898 | 1.0 | — | — | — | — |
| Toluene | 0.73 | — | — | 0.69 | 0.74 | — | 0.80 | 0.89 | — | — | — | — |
| Ethylbenzene | 78.32 | — | — | 73.74 | 62.99 | — | 67.35 | 75.24 | — | — | — | — |
| Xylene | 20.07 | — | — | 18.90 | 18.46 | — | 19.74 | 22.06 | — | — | — | — |
| C9 Aromatics | 0.82 | — | — | 0.77 | 0.52 | — | 0.56 | 0.63 | — | — | — | — |
| MDEB | 0.01 | — | — | 0.01 | 0.06 | — | 0.064 | <0.01 | 0.61 | 0.61 | 0.68 | 0.01 |
| PDEB | 0.01 | — | — | 0.01 | 9.45 | — | 10.11 | <0.01 | 96.25 | 96.25 | 99.23 | 4.89 |
| ODEB | <0.01 | — | — | <0.01 | 0.01 | — | 0.01 | <0.01 | 0.095 | 0.095 | 0.06 | 0.1 |
| C10 + Heavy Aromatics | 0.06 | — | — | 0.06 | 0.30 | — | 0.32 | <0.01 | 3.045 | 3.045 | 0.03 | 95.0 |
| Sulfur (ppm) | <1 | | | <1 | | — | | | <1 | <1 | <1 | <1 |
| Chloride (ppm) | <1 | | | <1 | | — | | | <1 | <1 | <1 | <1 |
| Carbonyl (ppm) | <1 | | | <1 | | — | | | <1 | <1 | <1 | <1 |
| Bromine Index | <1 | | | <1 | | — | 155 | — | 235 | <20 | <5 | — |

We claim:

1. A process for the production of para-diethyl benzene from a mixed aromatic feedstock comprising: (a) ethylbenzene, (b) at least one other aromatic or non-aromatic compound wherein the aromatic compound is selected from the group consisting of benzene, alkylated benzene having alkyl group with carbon number 1 to 6, mono-alkyl aromatics, dialkyl aromatics, trialkyl aromatics, tetraalkyl aromatics, pentaalkyl aromatics, hexaalkyl aromatics, and a mixture thereof, and the non-aromatic compound is selected from the group consisting of any isomers having carbon number in the range of $C_1$-$C_{11}$ and a mixture there of, and (c) optionally an ethylating agent, said process comprising following the steps in sequence of:

(i) contacting the feedstock under conditions sufficient to affect the conversion by disproportionation and alkylation of ethylbenzene, and optionally in presence of a carrier gas selected at least one from nitrogen, hydrogen, steam or a mixture thereof, with a selectivated metallosilicate composite catalyst wherein said selectivated metallosilicate composite catalyst is prepared by (i) contacting an intermediate pore metallosilicate extrudate with water soluble or water insoluble organosilicon compound in a solvent selected from the group consisting of lower aliphatic alcohols, $C_5$-$C_{10}$ saturated linear or cyclic hydrocarbons, $C_6$-$C_8$ aromatics or mixture thereof, for 0.5 to 48 hours, and then recovering the solvent;

(ii) combining the organosilicon compound treated metallosilicate with 1 to 200 percent of the mass of the metallosilicate of water or water vapor, and then drying the catalyst at a temperature of from 80 to 130° C. for from 1 to 20 hours;

(iii) repeating the steps (i) and (ii) for any number of times; and (iv) calcining the catalyst in an oxygen containing atmosphere sufficient to remove the organic material and to deposit siliceous matter on the metallosilicate at a temperature in the range of from 160 to 800° C. for 2 to 20 hours wherein the calcining step is not repeated after each intermediate of steps (i) and (ii); and (2) recovering a product stream containing at least 95 wt % para-diethyl benzene, the product stream being substantially free from other isomers of diethylbenzene, $C_8$ aromatics, $C_9$ aromatics, $C_{10+}$ heavy aromatics other than diethylbenzene isomers; sulphur, halogen, olefinic compound and carbonyl compounds wherein the reactor effluent from step (1) or the pure recovered product from step (2) or an intermediate crude product stream containing at least 88 weight percent para-diethylbenzene along with heavy hydrocarbons of carbon number 10 or above is contacted with a clay material selected from the group consisting of montmorillonite, bentonite, attapulgite and a mixture thereof.

2. The process as claimed in claim 1, wherein the ethylbenzene content in the feedstock is in the range of 20 to 95 wt %.

3. The process as claimed in claim 1, wherein the feedstock contains aromatic compounds other than ethylbenzene in the range of 50 to 80 wt %.

4. The process as claimed in claim 1, wherein said other aromatic compounds comprise a mixture of xylene isomers in the range of 0.05 to 80 wt %.

5. The process as claimed in claim 1, wherein said feedstock contains benzene or toluene in the range of about 0.05 to 5 wt %.

6. The process as claimed in claim 1, wherein said feedstock contains isomers of $C_9$ aromatic hydrocarbons in the range of 0.05 to 5 wt %.

7. The process as claimed in claim 1, wherein said feedstock contains non-aromatic hydrocarbons having carbon number 1 to 11, in a range of 0.05 to 6 wt %.

8. The process as claimed in claim 1, wherein the molar ratio of said aromatic hydrocarbon to the ethylating moiety, is in the range of from 20:1 to 0.1:1.

9. The process as claimed in claim 1, wherein said feedstock is passed over said selectivated metallosilicate composite catalyst at a temperature of from 240° C. to 700° C., at a pressure of from 0.1 atm, to 200 atm, and at weight hourly space velocity of from 0.1 per hour to 50 per hour.

10. The process as claimed in claim 1, wherein the alkyl aromatic feed stock is selected from the group consisting of by-product of naphtha cracker unit containing $C_8$ aromatics and mixed xylene solvent called pyrolysis gasoline, or pygas xylene stream.

11. The process as claimed in claim 1, wherein the at least one ethylating agent is selected from the group consisting of ethylene, ethanol, ethyl chloride, ethyl sulphate and diethyl ether and a mixture thereof.

12. The process as claimed in claim 1, wherein the carrier gas concentration expressed in terms of carrier gas to aromatic hydrocarbon feed mole ratio is in the range of 0.1 to 40.

13. The process as claimed in claim 1, wherein said composite catalyst is a selectivated galloaluminosilicate.

14. The process as claimed in claim 1, wherein the water insoluble organosilicon compound used for preparing said composite catalyst is tetra-alkoxy silane.

15. The process as claimed in claim 1, wherein the water soluble organosilicon compound used for preparing said composite catalyst is aminoalkyltrialkoxy silane.

16. The process as claimed in claim 1, wherein the metallosilicate used for preparing said composite catalyst is selected from the group consisting of Ga—ZSM-5, Fe—ZSM-5, B—ZSM-5, Al—ZSM-5, Ga—Al—ZSM-5, Fe—Al—ZSM-5 and B—Al—ZSM-5.

17. The process as claimed in claim 1, wherein said metallosilicate is Ga—Al—ZSM-5 having silicon to aluminum ratio in the range of 150 to 600 and silicon to gallium ratio in the range of 500 to 2000.

18. The process as claimed in claim 1, wherein said metallosilicate has a crystallite size of at least 1 micron.

19. The process as claimed in claim 1, wherein the metallosilicate composite catalyst contains a binder selected from the group consisting of alumina, silica, clay or a mixture thereof in the range of 10-90 wt % wherein the clay is selected from the group consisting of at least one of montmorillonite, bentonite, attapulgite and a mixture thereof.

20. The process as claimed in claim 19, wherein the clay for clay treatment is acid activated bentonite.

21. The process as claimed in claim 19, wherein the clay treatment is carried out at a temperature of from 20° C. to 300° C., at a pressure of from 0.1 atm. to 70 atm., and at a liquid hourly space velocity of from 0.1 per hour to 100 per hour.

22. The process as claimed in claim 1, wherein the final para-diethylbenzene product has unsaturated hydrocarbon content expressed in terms of Bromine Index of less than 20.

23. The process as claimed in claim 1, wherein the para-diethylbenzene product has a carbonyl compound content of less than 1 ppm.

24. The process according to claim 1, wherein the solvent is methanol or toluene.

25. The process according to claim 11, wherein the ethylating agent is ethylene.

26. The process according to claim 15, wherein the aminoalkyltrialkoxy silane is 3-amiopropyl triethoxysilane.

27. The process according to claim 14, wherein the tetraalkoxy silane is tetraethoxysilane.

* * * * *